(12) United States Patent
Javet et al.

(10) Patent No.: US 6,793,687 B2
(45) Date of Patent: Sep. 21, 2004

(54) DIAMINOPYRAZOLE DERIVATIVES AND OXIDATION HAIR DYES CONTAINING PYRAZOLONE DERIVATIVES

(75) Inventors: Manuela Javet, Marly (CH); Christel Dousse, Courtepin (CH); Dominique Le Cruer, Marly (CH)

(73) Assignee: Wella Aktiengesellschaft, Darmstadt (DE)

( * ) Notice: Subject to any disclaimer, the term of this patent is extended or adjusted under 35 U.S.C. 154(b) by 45 days.

(21) Appl. No.: 10/257,101

(22) PCT Filed: Sep. 13, 2001

(86) PCT No.: PCT/EP01/10585

§ 371 (c)(1), (2), (4) Date: Oct. 8, 2002

(87) PCT Pub. No.: WO02/069918

PCT Pub. Date: Sep. 12, 2002

(65) Prior Publication Data

US 2003/0131423 A1 Jul. 17, 2003

(30) Foreign Application Priority Data

Mar. 1, 2001 (DE) .......................... 101 09 806

(51) Int. Cl.$^7$ ................................. A61K 7/13
(52) U.S. Cl. ..................... 8/405; 8/406; 8/408; 8/409; 8/570; 8/573; 8/576; 8/649; 8/668; 8/669; 8/670
(58) Field of Search ............................ 8/405, 406, 408, 8/409, 570, 573, 576, 649, 668, 669, 670

(56) References Cited

U.S. PATENT DOCUMENTS 6,074,438 A  *  6/2000  Lim et al. ..................... 8/409

FOREIGN PATENT DOCUMENTS

| DE | 42 34 885 A1 | 4/1994 |
| DE | 42 34 887 A1 | 4/1994 |
| DE | 197 30 412 C1 | 12/1998 |
| DE | 199 16 033 A | 10/2000 |
| DE | 200 13 156 U | 10/2000 |
| EP | 0 375 977 A1 | 7/1990 |
| EP | 0 740 931 A1 | 11/1996 |

* cited by examiner

Primary Examiner—Brian P. Mruk
Assistant Examiner—Eisa Elhilo
(74) Attorney, Agent, or Firm—Michael J. Striker

(57) ABSTRACT

The object of the invention is an agent for oxidatively dyeing keratin fibers, wherein it contains (a) at least one 4,5-diaminopyrazole derivative of Formula (I), (II) or (III) or its salt with organic or inorganic acids,

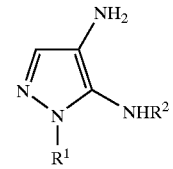

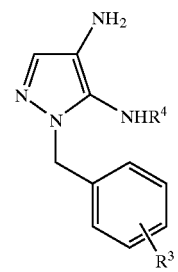

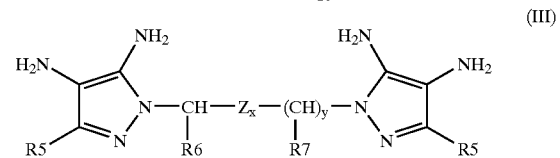

as well as
(b) at least one pyrazol-5-one derivative of the general formula (IV), (V) or (VI), or its salt with organic or inorganic acids,

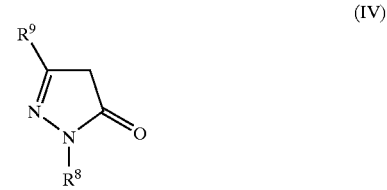

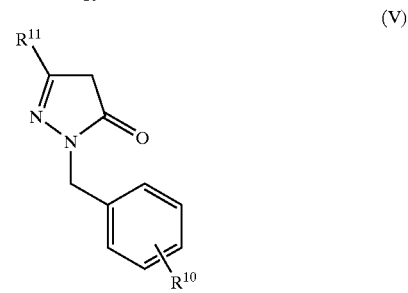

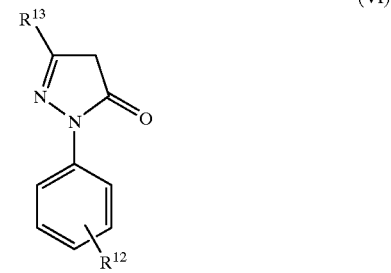

9 Claims, No Drawings

DIAMINOPYRAZOLE DERIVATIVES AND OXIDATION HAIR DYES CONTAINING PYRAZOLONE DERIVATIVES

BACKGROUND OF THE INVENTION

The object of the present Invention are agents for oxidatively dyeing hair, which contain certain diaminopyrazole derivatives as developer substance and certain pyazolone derivatives as coupler substance.

Hair dyeing agents are divided mainly into oxidation dyeing agents and non-oxidative tinting, depending on the starting color of the hair, which is to be dyed, and on the desired end result. At the present time, oxidative hair dyes have attained a significant importance. The dyeing is brought about here by the reaction of certain developer substances with certain coupler substances in the presence of suitable oxidizing agents.

As developer substances, particularly 2,5-diaminotoluene, 2.5-diaminophenylethyl alcohol, p-aminophenol and 1,4-diaminobenzene are used. Frequently used coupler compounds are resorcinol, 1-naphthol, 3-aminophenol, 5-amino-2-methylphenol, 4-chlororesorcinol and derivatives of m-phenylenediamine.

Oxidation dyes, which are used to dye human hair, must fulfill numerous requirements. They must be physiologically compatible and provide dyeings in the desired intensity. In addition, the hair dyeings should be highly resistant to the effects of light, permanent waving agents and acids, as well as friction, and remain stable for at least 4 to 6 weeks under normal conditions.

In addition, an oxidative dyeing system must make possible a wide range of different color nuances in the range of natural shades as well as of fashion shades. This means that, on the one hand, yellow, red and blue dyes must be available for the fashion shade range and, on the other, blond, brown and black dyes for the natural shade range. The natural shades can also be obtained by mixing different dyes, which produce yellow, red and blue.

As developer substances in the fashion shade range, 4,5-diaminopyrazole derivatives, which are tolerated well physiologically, have gained acceptance recently. They produce very intensive red, violet and blue color shades with different coupler compounds. Such oxidation dyeing agents, which contain pyrazoles, are described, for example, in the DE-OS 42 34 885, DE-OS 42 34 887, DE-PS 197 30 412, EP-OS 0 375 977 and the EP-OS 0 740 931.

Color nuances in the yellow and orange range have not previously been described with the pyrazole derivatives named above.

SUMMARY OF THE INVENTION it is therefore an object of the present invention to make available a system of developer and coupler substances, which is suitable for the yellow and orange color ranges and contains certain diaminopyrazole derivatives as developer substance.

It has now been discovered that this objective can be accomplished by using certain pyrazolone derivatives as coupler substance.

The object of the present invention therefore is an agent for the oxidative dyeing of keratin fibers, especially of hair, wherein the agent contains (a) at least one 4,5-diaminopyrazole derivative of Formula (I), (II) or (III) or its salt with organic or inorganic acids,

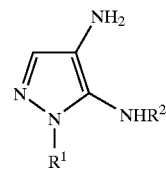

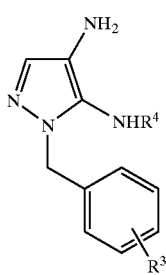

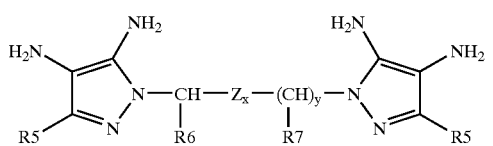

wherein R1 and R2 independently of one another represent hydrogen, a linear or branched $C_1$–$C_6$ alkyl group, an optionally substituted phenyl group or a linear or branched $C_2$–$C_4$-hydroxyalkyl group;

R3 represents a halogen atom (F, Cl, Br, I), a linear or branched $C_1$–$C_4$ alkyl group or a linear or branched $C_1$–$C_4$ alkoxy group and R4 represents hydrogen, a linear or branched $C_1$–$C_4$ alkyl group or a linear or branched $C_2$–$C_4$ hydroxyalkyl group;

R5 represents hydrogen, a linear or branched $C_1$–$C_6$ alkyl group, a $C_1$–$C_4$ hydroxy alkyl group, a $C_1$–$C_4$ aminoalkyl group, a $C_1$–$C_8$ alkylamino group, a di($C_1$–$C_8$) alkylamino group, a $C_1$–$C_4$ alkylamino-($C_1$–$C_4$)alkyl group or a di($C_1$–$C_4$) alkylamino-($C_1$–$C_4$)alkyl group, an aryl group or a heteroaryl group;

R6 and R7 may be identical or different and represent hydrogen, a linear or branched $C_1$–$C_6$ alkyl group, an aryl group, a heteroaryl group, a carboxylic acid group, a carboxylic ester group, an unsubstituted or substituted carboxylic acid amide group, a hydroxy group or a $C_1$–$C_4$ hydroxyalkyl group or R2 and R3 jointly form an optionally substituted $C_1$–$C_6$ alkylene group;

Z is a $C_1$–$C_{10}$ alkyl diradical, which is optionally interrupted by a hetero atom (such as a nitrogen, oxygen or sulfur atom), an aromatic or heteroaromatic diradical, which is optionally condensed with one or two benzene rings and/or substituted by a hydroxy group or a $C_1$–$C_6$ alkyl group, or a diradical of formula —Ar-(Alk)$_n$-Ar—, in which Ar is an optionally substituted aryl or heteroaryl group, especially a phenylene or pyridyl group, Alk is a —$CH_2$ group and n is a whole number from 0 to 6; and x and y independently of one another are equal to 0 or 1;

and (b) at least one pyrazol-5-one derivative of the general Formula (IV), (V) or (VI), especially (IV) or (VI), or its salt with organic or inorganic acids,

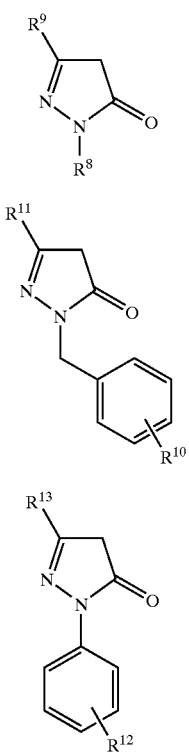

wherein
R8 is a linear or branched $C_1-C_4$ alkyl group, a linear or branched $C_1-C_4$ alkoxy group, a linear or branched $C_1-C_4$ alkoxy-$(C_1-C_8)$alkyl group or a linear or branched $C_2-C_4$ hydroxyalkyl group; and
R9 to R13 independently of one another in each case are hydrogen, a linear or branched $C_1-C_4$ alkyl group, a linear or branched $C_2-C_4$ hydroxyalkyl group, a hydroxy group, an amino group, a linear or branched $C_1-C_4$ alkoxy group, a linear or branched $C_1-C_4$ alkoxy-$(C_1-C_4)$alkyl group or a $C_1-C_4$ hydroxyalkylamino group.

In particular, the following may be mentioned as preferred 4,5-diaminopyrazole derivatives of Formulas (I), (II) and (III): 4,5-diamino-1-methyl-1H-pyrazole; 4,5-diamino-1-(4'-methylbenzyl)-pyrazole; 4,5-diamino-1-(3'-methylbenzyl)-pyrazole; 4,5-diamino-1-(2'-methylbenzyl)-pyrazole; 4,5-diamino-1-(2'-hydroxyethyl)-1H-pyrazole; 4,5-diamino-1-benzyl-1H-pyrazole; 4,5-diamino-1-ethyl-1H-pyrazole; 4,5-diamino-1-isopropyl-1H-pyrazole; 4,5-diamino-1-pentyl-1H-pyrazole; 4,5-diamino-1-(4'-methoxybenzyl)-1H-pyrazole; 4,5-diamino-1H-pyrazole; 4,5-diamino-1-(3'-methoxybenzyl)-1H-pyrazole; 4,5-diamino-1-(2'-methoxybenzyl)-1H-pyrazole; 4,5-diamino-1-(4'-chlorobenzyl)-1H-pyrazole; 4,5-diamino-1-(3'-chlorobenzyl)-1H-pyrazole; 4,5-diamino-1-(2'-chlorobenzyl)-1H-pyrazole; 4-amino-5-methylamino-1-(4'-methoxybenzyl)-1H-pyrazole; 4-amino-5-(2'-hydroxyethyl)amino-1-(4'-methoxybenzyl)-1H-pyrazole; 4-amino-5-methylamino-1-(2'-hydroxyethyl)-1H-pyrazole; bis-(4,5-diamino-pyrazole-1-yl)-methane; 1,2-bis-(4,5-diamino-pyrazole-1-yl)-ethane; 1,3-bis-(4,5-diamino-pyrazole-1-yl)-propane, 1,3-bis-(4,5-diamino-3-phenyl-pyrazole-1-yl)-propane; 2,3,-bis-(4,5-diamino-pyrazole-1-yl)-propane-1-ol; N-benzyl-2,3-bis-(4,5-diamino-pyrazole-1-yl)-propionamide; 1,3-bis-(4,5-diamino-pyrazole-1-yl)-cyclohexane; 1,4-bis-(4,5-diamino-pyrazole-1-yl-methyl)-benzene; 1,4-bis-(4,5-diamino-pyrazole-1-yl-methyl)-2,5-dimethoxy-benzene; 1,3-bis-(4,5-diamino-pyrazole-1-yl-methyl)-benzene; 2,6-bis-(4,5-diamino-pyrazole-1-yl-methyl)-4-methyl-phenol; 1,2-bis-(4,5-diamino-pyrazole-1-yl-methyl)-benzene; 1,2-bis-(4,5-diamino-pyrazole-1-yl-methyl)-4,5-dimethoxy-benzene; 2,3-bis-(4,5-diamino-pyrazole-1-yl-methyl)-naphthalene; 2,3-bis-(4,5-diamino-pyrazole-1-yl-methyl)-anthracene; 9,10-bis-(4,5-diamino-pyrazole-1-yl-methyl)-anthracene; 4,4'-bis-(4,5-diamino-pyrazole-1-yl-methyl)-biphenyl; 1,2-bis-[4-(4,5-diamino-pyrazole-1-yl-methyl)-phenyl]-ethane; 2,5-bis-(4,5-diamino-pyrazole-1-yl-methyl)-furan; 2,5-bis-(4,5-diamino-pyrazole-1-yl-methyl)-thiophene; 2,8-bis-(4,5-diamino-pyrazole-1-yl-methyl)-dibenzothiophene; 4,4'-bis-(4,5-diamino-pyrazole-1-yl-methyl)-[2,2']bipyridyl and 1,2-bis-[6-(4,5-diamino-pyrazole-1-yl-methyl)-pyridine-2-yl]-ethane or their salts with organic and inorganic acids.

In particular, the following may be mentioned as preferred pyrazolone derivatives of Formulas (IV), (V) and (VI): 3-amino-1-phenyl-pyrazole-5-one, 3-methyl-1-phenyl-pyrazole-5-one, 1,3-dimethyl-pyrazole-5-one, 3-methyl-1-(4-sulfphenyl)-pyrazole-5-one, 3-methyl-1-(2-hydroxyethyl)-pyrazole-5-one and 1-phenyl-pyrazole-5-one or their salts with organic or inorganic acids.

The 4,5-diaminopyrazole of Formula (I), (II) or (III), as well as the pyrazolone derivative of Formula (IV), (V) or (VI) is contained in the inventive dyeing agents in each case in a total amount of about 0.005 to 20 percent by weight, an amount of 0.01 to 10 percent by weight and, in particular, of 0.1 to 6 percent by weight being preferred.

Aside from the above-mentioned 4,5-diaminopyrazole derivatives, the inventive agent may also contain further developer substances. Particularly suitable for this purpose are 1,4-diamino-benzene (p-phenylenediamine), 1,4-diamino-2-methylbenzene (p-toluylenediamine), 1,4-diamino-2,6-dimethylbenzene, 1,4-diamino-2,5-dimethylbenzene, 1,4-diamino-2,3-dimethylbenzene, 2-chloro-1,4-diaminobenzene, 4-phenyl-amino-aniline, 4-dimethylamino-aniline, 4-diethylamino-aniline, 4-[di(2-hydroxyethyl)amino]-aniline, 4-[(2-methoxyethyl)amino]-aniline, 4-[(3-hydroxypropyl)amino]-aniline, 1,4-diamino-2-(2-hydroxyethyl)-benzene, 1,4-diamino-2-(1-hydroxyethyl)-benzene, 1,4-diamino-2-(1-methylethyl)-benzene, 1,3-bis[(4-aminophenyl)-(2-hydroxyethyl)amino]-2-propanol, 1,8-bis(2,5-diaminophenoxy)-3,6-dioxaoctane, 4-amino-phenol, 4-amino-3-methyl-phenol, 4-methylamino-phenol, 4-amino-2-(aminomethyl)-phenol, 4-amino-2-[(2-hydroxyethyl)-amino]methyl-phenol, 4-amino-2-(methoxy-methyl)-phenol, 4-amino-2-(2-hydroxyethyl)-phenol, 5-amino-salicylic acid, 2,5-diamino-pyridine, 2,4,5,6-tetraamino-pyrimidine, 2,5,6-triamino-4-(1H)-pyrimidone, 2-amino-phenol, 2-amino-6-methyl-phenol and 2-amino-5-methyl-phenol or their salts.

Aside from the 2-pyrazolone-5-one derivatives, the dye carrier composition may also contain further coupler substances, which are suitable for forming an oxidation dye. Aromatic m-diamines, m-aminophenols, polyphenols or naphthols may be used for this purpose. Particularly suitable are N-(3-dimethylamino-phenyl)-urea, 2,6-diamino-pyridine, 2-amino-4-[(2-hydroxyethyl)-amino]-anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxy-ethyl)amino]-1,5-dimethoxybenzene, 2,3-diamino-6-methoxy-pyridine, 3-amino-6-methoxy-2-(methylamino)-pyridine, 2,6-diamino-3,5-dimethoxy-pyridine, 3,5-diamino-2,6- dimethoxy-pyridine, 1,3-diaminobenzene, 2,4-diamino-1-(2-hydroxyethoxy)-benzene, 2,4-diamino-1-(3-hydroxypropoxy)-benzene, 2,4-diamino-1-(3-methoxypropoxy)-benzene, 1-(2-aminoethoxy)-2,4-diaminobenzene, 2-amino-1-(2-hydroxyethoxy)-4-methylaminobenzene, 2,4-diaminophenoxy-acetic acid, 3-[di(2-hydroxyethyl)amino]-aniline, 4-amino-2-di[(2-hydroxyethyl)amino]-1-ethoxybenzene, 5-methyl-2-(1-methylethyl)-phenol, 3-[(2-hydroxyethyl)amino]-aniline, 3-[(2-aminoethyl)-amino]-aniline, 1,3-di(2,4-diaminophenoxy)-propane, di(2,4-diaminophenoxy)-methane, 1,3-diamino-2,4-dimethoxybenzene, 2,6-bis(2-hydroxyethyl)amino-toluene, 4-hydroxyindole, 3-dimethylamino-phenol, 3-diethylamino-phenol, 5-amino-2-methyl-phenol, 5-amino-4-fluoro-2-methyl-phenol, 5-amino-4-methoxy-2-methyl-phenol, 5-amino-4-ethoxy-2-methyl-phenol, 3-amino-2,4-dichloro-phenol, 5-amino-2,4-dichloro-phenol, 3-amino-2-methyl-phenol, 3-amino-2-chloro-6-methyl-phenol, 3-amino-phenol, 2-[(3-hydroxyphenyl)-amino]-acetamide, 5-[(2-hydroxy-ethyl)amino]-2-methyl-phenol, 3-[(2-hydroxyethyl)amino]-phenol, 3-[(2-methoxyethyl)amino]-phenol, 5-amino-2-ethyl-phenol, 2-(4-amino-2-hydroxyphenoxy)-ethanol, 5-[(3-hydroxypropyl)amino]-2-methyl-phenol, 3-[(2,3-dihydroxypropyl)-amino]-2-methyl-phenol, 3-[(2-hydroxyethyl)-amino]-2-methyl-phenol, 2-amino-3-hydroxy-pyridine, 5-amino-4-chloro-2-methyl-phenol, 1-naphthol, 1,5-dihydroxy-naphthalene, 1,7-dihydroxy-naphthalene, 2,3-dihydroxy-naphthalene, 2,7-dihydroxy-naphthalene, 2-methyl-1-naphthol-acetate, 1,3-dihydroxy-benzene, 1-chloro-2,4-dihydroxy-benzene, 2-chloro-1,3-dihydroxy-benzene, 1,2-dichloro-3,5-dihydroxy-4-methyl-benzene, 1,5-dichloro-2,4-dihydroxy-benzene, 1,3-dihydroxy-2-methyl-benzene, 1,3-dihydroxy-2,4-dimethyl-benzene, 3,4-methylenedioxy-phenol, 3,4-methylenedioxy-aniline, 5-[(2-hydroxyethyl)-amino]-1,3-benzodioxol, 6-bromo-1-hydroxy-3,4-methylenedioxybenzene, 3,4-diamino-benzoic acid, 3,4-dihydro-6-hydroxy-1,4(2H)-benzooxazine, 6-amino-3,4-dihydro-1,4(2H)-benzooxazine, 5,6-dihydroxy-indole, 5,6-dihydroxy-indoline, 4-hydroxy-indole, 5-hydroxy-indole, 6-hydroxy-indole, 7-hydroxy-indole and 2,3-indolindione, or their salts.

The aforementioned, additional developer and coupler substances are contained in the dyeing agent in each case in a total amount of about 0.01 to 20 percent by weight, preferably of 0.1 to 10 percent by weight and, in particular, of 0.1 to 5 percent by weight.

Furthermore, the dyeing agent optionally may contain additional, conventional, substantive, anionic, cationic. zwitterionic or nonionic dyes. The preferred anionic dyes include, for example, 6-hydroxy-5-[(4-sulfophenyl)azo]-2-naphthalene disodium sulfonate (CI15985; Food Yellow No. 3; FD&C Yellow No. 6), 2,4-dinitro-1-naphthol-7-disodium sulfonate (CI10316; Acid Yellow No. 1; Food Yellow No. 1), 2-(indane-1,3-dione-2-yl)quinoline-x,x-sulfonic acid (mixture of mono and disulfonic acid) (CI47005; D&C Yellow No. 10; Food Yellow No. 13, Acid Yellow No. 3), trisodium 5-hydroxy-1-(4-sulfophenyl)-4-[(4-sulfophenyl)azo]-pyrazole-3-carboxylate (CI19140; Food Yellow No 4; Acid Yellow No. 23), 9-(2-carboxyphenyl)-6-hydroxy-3H-xanthene-3-one (CI45350; Acid Yellow No. 73; D&C Yellow No. 8), 5-[(2,4-dinitro-phenyl)amino]-2-phenylamino-sodium benzene sulfonate (CI10385; Acid Orange No. 3), 4-[(2,4-dihydroxyphenyl)azo]-monosodium benzene sulfonate (CI14270; Acid Orange No. 6), 4-[(2-hydroxynaphth-1-yl)azo]-sodium benzene sulfonate (CI15510; Acid Orange No. 7), 4-[(2,4-dihydroxy-3-[(2,4-dimethylphenyl)azo] phenyl)azo]-sodium benzene sulfonate (CI20170; Acid Orange No. 24), 4-hydroxy-3-[(4-sulfonaphth-1-yl)azo]-1-naphthalene-disodium sulfonate (CI14720; Acid Red No. 14), 6-hydroxy-5-[(4-sulfonaphth-1-yl)azo]-2,4-naphthalene-trisodium disulfonate (CI16255; Ponceau 4R; Acid Red No. 18), 3-hydroxy-4-[(4-sulfonaphth-1-yl)azo]-2,7-naphthalene-trisodium disulfonate (CI16185; Acid Red No. 27), 8-amino-1-hydroxy-2-(phenylazo)-3,6-naphthalene-disodium disulfonate (CI17200; Acid Red No. 33), 5-(acetylamino)-4-hydroxy-3-[(2-methylphenyl)-azo]-2,7-naphthalene-disodium disulfonate (CI18065; Acid Red No. 35), 2-(3-hydroxy-2,4,5,7-tetraiod-dibenzopyran-6-one-9-yl)-disodium benzoic acid (CI45430; Acid Red No. 51), N-[6-(diethylamino)-9-(2,4-disulfophenyl)-3H-xanthene-3-ylidene]-N-ethylethane aminium-hydroxide, internal salt, sodium (CI45100; Acid Red No. 52), 8-[(4-(phenylazo)-phenyl)azo]-7-naphthol-1,3-disodium disulfonate (CI27290; Acid Red No. 73), 2',4',5',7'-tetrabromo-3',6'-dihydroxyspiro[isobenzofuran-1(3H),9'-[9H]xanthene]-3-one-disodium (CI45380; Acid Red No. 87), 2',4',5',7'-tetrabromo-4,5,6,7-tetrachloro-3',6'-dihydroxyspiro [isobenzofuran-1(3H),9'[9H]xanthene]-3-one-disodium (CI45410; Acid Red N. 92), 3',6'-dihydroxy-4',5'-diiodospiro-[isobenzofuran-1(3H),9'(9H)-xanthene)-3-one-disodium (CI45425; Acid Red No. 95), (2-sulfophenyl)di[4-(ethyl((4-sulfophenyl)methyl)amino)-phenyl]-carbenium-disodium, betaine (CI42090; Acid Blue No. 9; FD&C Blue No. 1), 1,4-bis[(2-sulfo-4-methylphenyl)amino]-9,10-anthraquinone-disodium (CI 61570; Acid Green No. 25), bis[4-(dimethylamino)-phenyl]-(3,7-disulfo-2-hydroxy-naphth-1-yl)carbenium internal salt, monosodium (CI44090; Food Green No. 4; Acid Green No. 50), bis[4-(diethylamino)phenyl](2,4-disulfophenyl)-carbenium internal salt, sodium (2:1) (CI42045; Food Blue No. 3; Acid Blue No. 1), bis[4-(diethylamino)phenyl](5-hydroxy-2,4-disulfophenyl)-carbenium internal salt, calcium chloride (2:1) (CI42051; Acid Blue No. 3), 1-amino-4-(cyclohexylamino)-9,10-anthraquinone-2-sodium sulfonate (CI62045; Acid Blue No. 62), 2-(1,3-dihydro-3-oxo-5-sulfo-2H-indole-2-ylidene)-2,3-dihydro-3-oxo-1H-indole-5-disodium sulfonate (CI73015; Acid Blue No. 74), 9-(2-carboxyphenyl)-3-[(2-methylphenyl)-amino]-6-[(2-methyl-4-sulfophenyl)amino]xanthylium internal salt, monosodium (CI45190; Acid Violet No. 9), 1-hydroxy-4-[(4-methyl-2-sulfophenyl)amino]-9,10-anthraquinone sodium (CI60730; D&C Violet No. 2; Acid Violet No. 43), bis[3-nitro-4-[(4-phenylamino)-3-sulfo-phenylamino]-phenyl]-sulfone (CI10410; Acid Brown No. 13), 5-amino-4-hydroxy-6-[(4-nitrophenyl)azo]-3-(phenylazo)-2,7-naphthalene disodium disulfonate (CI20470; Acid Black No. 1), 3-hydroxy-4-[(2-hydroxynaphth-1-yl)azo]-7-nitro-1-naphthalene sulfonate chromium complex (3:2) (CI15711; Acid Black No. 52), 3-[(2,4-dimethyl-5-sulfophenyl)azo]-4-hydroxy-1-naphthalene disodium sulfonate (CI14700; Food Red No. 1; Ponceau SX; FD&C Red No. 4), 4-(acetylamino)-5-hydroxy-6-[(7-sulfo-4-[(4-sulfophenyl)azo]naphth-1-yl) azo]-1,7-naphthalene tetrasodium disulfonate (CI28440; Food Black No. 1) and 3-hydroxy-4-(3-methyl-5-oxo-1-phenyl-4,5-dihydro-1H-pyrazole-4-ylazo)-naphthalene-1-sodium sulfonate chromium complex (Acid Red No. 195).

The preferred cationic dyes include, for example, 9-(dimethylamino)-benzo[a]phenoxazine-7-ium chloride (CI51175; Basic Blue No. 6), di[4-(diethylamino)phenyl][4-(ethylamino)naphthyl]carbenium chloride (CI42595; Basic Blue No. 7), 3,7-di(dimethylamino)phenothiazine-5-ium chloride (CI52015; Basic Blue No. 9), di[4-(dimethylamino) phenyl][4-(phenylamino)-naphthyl]carbenium chloride (CI44045; Basic Blue No. 26), 2-[(4-(ethyl(2-hydroxyethyl)amino)phenyl)-azo]-6-methoxy-3-methyl-benzothiazolium methyl sulfate (CI11154; Basic Blue No. 41), 8-amino-2-bromo-5-hydroxy-4-imino-6-[(3-(trimethylammonio)phenyl)amino]-1(4H)-naphthalinone chloride (CI56059; Basic Blue No. 99), bis[4-(dimethylamino)-phenyl][4-(methylamino)phenyl]-carbenium chloride (CI42535; Basic Violet No. 1), tris(4-amino-3-methylphenyl)-carbenium chloride (CI42520; Basic Violet No. 2), tris[4-(dimethylamino)-phenyl]carbenium chloride (CI42555; Basic Violet No. 3), 2-[3,6-(diethylamino)dibenzopyranium-9-yl]-benzoic acid chloride (CI45170; Basic Violet No. 10), di(4-aminophenyl)(4-amino-3-methylphenyl)carbenium chloride (CI42510; Basic Violet No. 14), 1,3-bis[(2,4-diamino-5-methylphenyl)azo]-3-methylbenzene (CI21010; Basic Brown No. 4), 1-[(4-aminophenyl)azo]-7-(trimethylammonio)-2-naphthol chloride (CI12250; Basic Brown No. 16), 1-[(4-amino-2-nitrophenyl)azo]-7-(trimethylammonio)-2-naphthol chloride (CI12251; Basic Brown No. 17), 1-[(4-amino-3-nitro-phenyl)azo]-7-(trimethylammonio)-2-naphthol chloride (CI12251; Basic Brown No. 17), 3,7-diamino-2,8-dimethyl-5-phenyl-phenazinium chloride (CI50240; Basic Red No. 2), 1,4-dimethyl-5-[(4-(dimethylamino)phenyl)azo]-1,2,4-triazolium chloride (CI11055; Basic Red No. 22), 2-hydroxy-1-[(2-methoxy-phenyl)azo]-7-(trimethylammonio)-naphthalene chloride (CI12245; Basic Red No. 76), 2-[2-((2,4-dimethoxy-phenyl)amino)ethenyl]-1,3,3-trimethyl-3H-indole-1-ium chloride (CI48055; Basic Yellow No. 11), 3-methyl-1-phenyl-4-[(3-(trimethylammonio)phenyl)-azo]-pyrazole-5-one chloride (CI12719; Basic Yellow No. 57) and bis[4-(diethylamino)phenyl]phenylcarbenium hydrogen sulfate (1:1) (CI42040; Basic Green No. 1).

As suitable nonionic dyes, especially for improved color equalization and for producing special nuances, the following, for example, may be mentioned: 1-amino-2-[(2-hydroxyethyl)amino]-5-nitrobenzene (HC Yellow No. 5), 1-(2-hydroxyethoxy)-2-[(2-hydroxyethyl)-amino]-5-nitrobenzene (HC Yellow No. 4), 1-[(2-hydroxyethyl)amino]-2-nitrobenzene (HC Yellow No. 2), 2-[(2-hydroxyethyl)amino]-1-methoxy-5-nitrobenzene, 2-amino-3-nitro-phenol, 1-(2-hydroxyethoxy)-3-methylamino-4-nitrobenzene, 2,3-(dihydroxy-propoxy)-3-methylamino-4-nitrobenzene, 2-[(2-hydroxyethyl)amino]-5-nitrophenol (HC Yellow No. 11), 3-[(2-amino-ethyl)amino]-1-methoxy-4-nitrobenzene-hydrochloride (HC Yellow No. 9), 1-[(2-ureidoethyl)amino]-4-nitrobenzene, 4-[(2,3-dihydroxypropyl)amino]-3-nitro-1-trifluoromethylbenzene (HC Yellow No. 6), 1-chloro-2,4-bis-[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)-amino]-3-nitrobenzonitrile (HC Yellow No. 14), 4-[(2-hydroxyethyl)amino]-3-nitro-benzamide (HC Yellow No. 15), 1-amino-4-[(2-hydroxyethyl)amino]-2-nitrobenzene (HC Red No. 7), 2-amino-4,6-dinitro-phenol, 2-ethylamino-4,6-dinitrophenol, 4-amino-2-nitro-diphenylamine (HC Red No. 1), 1-amino-4-[di(2-hydroxyethyl)amino]-2-nitrobenzene-hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-amino-3-nitrophenol, 4-[(2-hydroxyethyl)-amino]-3-nitrophenol, 1-[(2-aminoethyl)amino]-4-(2-hydroxyethoxy)-2-nitrobenzene (HC Orange No. 2), 4-(2,3-dihydroxy-propoxy)-1-[(2-hydroxy-ethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitro-phenol, 4-ethylamino-3-nitrobenzoic acid, 2-[(4-amino-2-nitrophenyl)amino]-benzoic acid, 2-chloro-6-methylamino-4-nitrophenol, 2-chloro-6-[(2-hydroxyethyl)amino]-4-nitrophenol, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 1,2,3,4-tetrahydro-6-nitroquinoxaline, 7-amino-3,4-dihydro-6-nitro-2H-1,4-benzooxazine (HC Red No. 14), 1,4-bis[(2-hydroxyethyl)amino]-2-nitrobenzene, 1-(2-hydroxyethyl)amino-2-nitro-4-[di(2-hydroxyethyl)amino]-benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene-hydrochloride (HC Blue No. 12), 4-[di(2-hydroxyethyl)amino]-1-[(2-methoxyethyl)amino]-2-nitrobenzene (HC Blue No. 11), 1-[(2,3-dihydroxy-propyl)amino]-4-[methyl-(2-hydroxyethyl)-amino]-2-nitrobenzene (HC Blue No. 10), 1-[(2,3-dihydroxypropyl)amino]-4-[ethyl-(2-hydroxyethyl)amino]-2-nitrobenzene-hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl)amino]-2-nitrobenzene (HC Blue No. 6), 2-((4-amino-2-nitrophenyl)amino)-5-dimethyl-aminobenzoic acid (HC Blue No. 13), 1,4-di[(2,3-dihydroxypropyl)amino]-9,10-anthraquinone, 1-[(2-hydroxyethyl)amino]-4-methylamino-9,10-anthraquinone (CI61505, Disperse Blue No. 3), 2-[(2-aminoethyl)amino]-9,10-anthraquinone (HC Orange No. 5), 1-hydroxy-4-[(4-methyl-2-sulfo-phenyl)amino]-9,10-anthraquinone, 1-[(3-aminopropyl)amino]-4-methyl-amino-9,10-anthraquinone (HC Blue No. 8), 1-[(3-aminopropyl)amino]-9,10-anthraquinone (HC Red No. 8), 1,4-diamino-2-methoxy-9,10-anthraquinone (CI62015, Disperse Red No. 11, Solvent Violet No. 26), 1,4-dihydroxy-5,8-bis[(2-hydroxyethyl)amino]-9,10-anthraquinone (CI62500, Disperse Blue No. 7, Solvent Blue No. 69), 1-[di(2-hydroxyethyl)amino]-3-methyl-4-[(4-nitrophenyl)azo]-benzene (CI11210, Disperse Red No. 17), 4-[(4-amino-phenyl)azo]-1-[di(2-hydroxyethyl)amino]-3-methylbenzene (HC Yellow No. 7), 2,6-diamino-3-[(pyridine-3-yl)azo]-pyridine, 2-((4-(acetylamino)phenyl)-azo)-4-methylphenol (CI11855; Disperse Yellow No. 3).

From the group of substantive dyes, special mention is given to 2-amino-4,6-dinitrophenol and 2-ethylamino-4,6-dinitrophenol and 2-[(2-hydroxyethyl)amino)-4,6-dinitrophenol, as well as to dyes of the general Formula (VII),

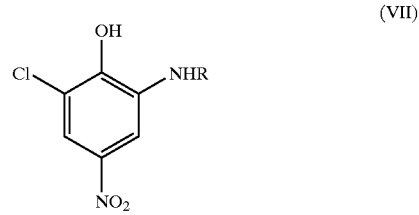

(VII)

in which R represents hydrogen, ethyl, methyl or hydroxyethyl.

The substantive dyes may be used in the dyeing agent in an amount of about 0.01 to 10 percent by weight and preferably of 0.1 to 5 percent by weight.

Of course, the dyes, insofar as they are bases, may also be used in the form of their physiologically tolerated salts with organic or inorganic acids, such as hydrochloric or sulfuric acid or, insofar as they have aromatic OH groups, in the form of the salts with bases, such as alkali phenolates.

The above-described, inventive combinations of combinations of compounds of Formulas (I) to (III) and (IV) to (VI), as well as, optionally, further oxidative hair-dyeing precursors and/or substantive dyes, are applied in a suitable dye carrier composition for the dyeing.

Moreover, the dyeing agent may contain further conventional additives, for example, antioxidants such as ascorbic acid, thioglycolic acid or sodium sulfite, as well as perfume oils, penetrants, buffer systems, complexing agents, preservatives, wetting agents, emulsifiers and care materials.

The inventive dyeing agent may be prepared, for example, in the form of a solution, especially an aqueous or an aqueous alcoholic solution. However, the particularly preferred forms of preparation are creams, gels or emulsions. Their composition represents a mixture of the dye components with conventional additives for such preparations.

Conventional additives in solutions, creams, emulsions or gels are, for example, solvents such as water, low molecular weight aliphatic alcohols, such as ethanol, n-propanol or isopropanol, glycerin or glycols such as 1,2-dihydroxypropane, furthermore wetting agents or emulsifiers from the classes of anionic, cationic, amphoteric or nonionic surface active substances, such as fatty alcohol sulfates, ethoxylated fatty alcohol sulfates, alkyl sulfonates, alkylbenzenesulfonates, alkyltrimethylammonium salts, alkyl betaines, ethoxylated fatty alcohols, ethoxylated nonylphenols, fatty acid alkanolamides and ethoxylated esters of fatty acids, furthermore thickeners such as higher molecular weight fatty alcohols, starch, cellulose derivatives, petrolatum, paraffin oil and fatty acids, as well as care materials, such as cationic resins, lanolin derivatives, cholesterol, pantothenic acid and betaine. The components mentioned are used in amounts, customary for such purposes; for example, the wetting agents and emulsifiers are used in concentrations of 0.1 to 30% by weight, the thickeners are used in an amount of about 0.1 to 30% by weight and the care materials are used in a concentration of about 0.1 to 5.0% by weight.

The ready-for-use inventive hair-dyeing agent is produced by mixing the dye carrier combination with an oxidizing agent immediately before these materials are applied.

As oxidizing agent, primarily hydrogen peroxide or its addition compounds with urea, melamine, sodium borate or sodium carbonate in the form of a 1 to 12% and preferably of 3 to 6% aqueous solution, comes into consideration. The ratio by weight of hair dyeing agent to oxidizing agent preferably is 5:1 to 1:3 and especially 1:1 to 1:2 here. Larger amounts of oxidizing agents are used especially for higher dye concentrations in the hair dyeing agent or if, at the same time, the hair is to be bleached more. In principle, it is also possible to use oxygen from the air instead of the aforementioned oxidizing agent to oxide the dye.

When the dye carrier composition (the pH of which is about 6 to 11.5) is mixed with the generally acidic oxidizing agent (the pH of which is about 2 to 6.5), the pH of the ready-for-use inventive hair dyeing agent adjusts to a value, which is determined by the amounts of alkali in the dye carrier composition and the amounts of acid in the oxidizing agent, as well as by the mixing ratio. Depending on the composition, the inventive dyeing agent may be weakly acidic, neutral or alkaline and, in the ready-for-use state, have a pH of about 3 to 11 and preferably of about 5 to 10. The pH is adjusted to a basic value here preferably with ammonia. However, organic amines, such as 2-amino-2-methyl-1-propanol, tris(hydroxymethyl)amino-methane, monoethanolamine and triethanolamine, or also inorganic bases such as sodium hydroxide and potassium hydroxide may also be used. For adjusting the pH to an acidic range, inorganic or organic acids, such as phosphoric acid, acetic acid, lactic acid, ascorbic acid, citric acid or tartaric acid come into consideration.

Subsequently, an amount of this mixture, which is sufficient for the dyeing treatment of the hair and, depending upon the fullness of the hair, ranges from about 60 to 200 gram, is applied on the hair and allowed to act for about 10 to 45 minutes and preferably for 30 minutes at a temperature preferably of 30° to 40° C. on the hair, after with the hair is rinsed with water and dried. Optionally, at the conclusion of this rinsing, the hair is washed with a shampoo and possibly rinsed with a weak organic acid, such as citric acid or tartaric acid. Subsequently, the hair is dried.

The dyeing agent, containing the inventive combination of 4,5-diaminopyrazoles of Formula (I), (II) or (III) and pyrazolone derivatives of Formula (IV), (V) or (VI), enables the hair to be dyed yellow to orange with outstanding color fastness, especially with regard to the light, washing and crocking fastness. The color shades are distinguished here especially by their color intensity and luminosity.

The following Examples are intended to explain the object in greater detail, without limiting it to these Examples.

EXAMPLES

Examples 1.1 to 1.7

Hair Dyeing Agent

| | |
|---|---|
| 4,5-Diaminopyrazole derivative of Formula (I) or (II) | Quantitative data in Table 1 |
| Pyrazole-5-one derivative of Formula (IV) or (VI) | Quantitative data in Table 1 |
| Sodium hydroxide (10% aqueous solution) | 0.74 g |
| Sodium sulfite | 0.40 g |
| Ascorbic acid | 0.30 g |
| Disodium ethylenediaminotetraacetate | 0.30 g |
| Lauryl ether sulfate, (28% aqueous solution) | 10.0 g |
| Ethanol | 8.00 g |
| Ammonia (25% aqueous solution) | 9.20 g |
| Water, fully desalinated | ad 100.00 g |

The above dye-carrier composition (5 g) is mixed with 5 g of a 6 percent hydrogen peroxide solution. The ready-for-use oxidation hair-dyeing agent obtained is applied on the strands of hair and distributed uniformly with a brush. After a period of action of 20 minutes at 40° C., the hair is rinsed with lukewarm water and then and dried.

The dyeing results are summarized in the following Table 1.

TABLE 1

| No. | Developer/Coupler Combination | Shade after the dyeing | | Measured Color Values of the Strands of Hair | | |
|---|---|---|---|---|---|---|
| | | | | L | a | b |
| 1.1 | 4,5-diamino-1-(2'-hydroxyethyl)-1H-pyrazole sulfate: 2.30 g; 3-methyl-1-phenyl-pyrazole-5-one: 1.74 g | warm yellow | Before the dyeing: After the dyeing: | +83.30; +59.16 | −0.48; +30.14; | +10.40 +51.54 |
| 1.2 | 4,5-diamino-1-(2'-hydroxyethyl)-1H-pyrazole sulfate: 2.30 g; 3-amino-1-phenyl-pyrazole-5-one: 1.74 g | yellow | Before the dyeing: After the dyeing: | +83.30; +60.94; | −0.48; +19.56; | +10.40 +48.59 |
| 1.3 | 4,5-diamino-1-(2'-hydroxyethyl)-1H-pyrazole sulfate: 2.30 g; 3-methyl-1-(4-sulfophenyl)-pyrazole-5-one: 2.54 g | yellow orange | Before the dyeing: After the dyeing: | +83.30; +51.54; | −0.48; +34.11; | +10.40 +37.34 |
| 1.4 | 4,5-diamino-1-(2'-hydroxyethyl)-1H-pyrazole sulfate: 2.30 g; 1,3-dimethyl-pyrazole-5-one: 1.12 g | yellow orange | Before the dyeing: After the dyeing: | +83.30; +58.29; | −0.48; +30.96; | +10.40 +45.53 |
| 1.5 | 4,5-diamino-1-(2'-hydroxyethyl)-1H-pyrazole sulfate: 2.30 g; 3-methyl-1-(2-hydroxyethyl)-pyrazole-5-one: 1.42 g | yellow orange | Before the dyeing: After the dyeing: | +83.30; +57.93; | −0.48; +29.73; | +10.40 +37.86 |
| 1.6 | 4,5-diamino-1-(4'-methylbenzyl)-1H-pyrazole sulfate: 2.41 g; 3-methyl-1-phenyl-pyrazole-5-one: 1.74 g | orange | Before the dyeing: After the dyeing: | +83.30; +56.25; | −0.48; +33.04; | +10.40 +51.02 |
| 1.7 | Developer: 4,5-diamino-1-(2'-hydroxyethyl)-1H-pyrazole sulfate: 2.30 g; Coupler: 3-amino-1-phenyl-pyrazole-5-one: 1.31 g; N-(3-(dimethylamino)phenyl)-urea: 0.42 4-amino-2-hydroxy-toluene: 0.008 g | brown | Before the dyeing: After the dyeing: | +83.30; +27.91; | −0.48; +22.30; | +10.40 +8.29 |

Examples 2.1 to 2.6

Hair Dyeing Preparation

| | |
|---|---|
| Bridged diaminopyrazole derivative of Formula (III) | Quantitative data in Table 1 |
| Pyrazole-5-one derivative of Formula (IV) or (IV) | Quantitative data in Table 1 |
| Sodium hydroxide (10% aqueous solution) | 0.74 g |
| Sodium sulfite | 0.40 g |
| Ascorbic acid | 0.30 g |
| Disodium ethylenediaminotetraacetate | 0.30 g |
| Lauryl ether sulfate, (28% aqueous solution) | 10.0 g |
| Ethanol | 8.00 g |
| Ammonia (25% aqueous solution) | 9.20 g |

-continued

| | |
|---|---|
| Water, fully desalinated | ad 100.00 g |

The above dye-carrier composition (5 g) is mixed with 5 g of a 6 percent hydrogen peroxide solution. The ready-for-use oxidation hair-dyeing agent obtained is applied on the strands of hair and distributed uniformly with a brush. After a period of action of 20 minutes at 40° C., the hair is rinsed with lukewarm water and then and dried.

The dyeing results are summarized in the following Table 1.

TABLE 1

| No. | Developer/Coupler Combination | Shade after the dyeing | | Measured Color Values of the Strands of Hair | | |
|---|---|---|---|---|---|---|
| | | | | L | a | b |
| 2.1 | 1,4-bis-(4,5-diamino-pyrazole-1-yl-methyl)-benzene: 4.28 g; 3-methyl-1-phenyl-pyrazole-5-one: 1.74 g | warm yellow | Before the dyeing: After the dyeing: Wash test: Dyeing result after 5 hours in demineralized water | +83.30; +57.05 +50.14; | −0.48; +31.30; +31.87; | +10.40 +50.43 +45.53 |
| 2.2 | 1,4-bis-(4,5-diamino-pyrazole-1-yl-methyl)-benzene: 4.28 g; 3-amino-1-phenyl-pyrazole-5-one: 1.75 g | yellow | Before the dyeing: After the dyeing: | +83.30; +63.78; | −0.48; +15.33; | +10.40 +53.29 |

TABLE 1-continued

| No. | Developer/Coupler Combination | Shade after the dyeing | Measured Color Values of the Strands of Hair | | |
|---|---|---|---|---|---|
| | | | L | a | b |
| | | Wash test: Dyeing result after 5 hours in demineralized water | +51.56; | +23.09; | +44.59 |
| 2.3 | 1,2-bis-(4,5-diamino-pyrazole-1-yl)-ethane: 3.52 g; 3-methyl-1-phenyl-pyrazole-5-one: 1.74 g | brown yellow | Before the dyeing: +83.30; After the dyeing: +54.04 | −0.48; +12.46; | +10.40 +36.56 |
| | | Wash test: Dyeing result after 5 hours in demineralized water | +45.86; | +15.44; | +32.04 |
| 2.4 | 1,2-bis-(4,5-diamino-pyrazole-1-yl)-ethane: 3.52 g; 3-amino-1-phenyl-pyrazole-5-one: 1.75 g | green yellow | Before the dyeing: +83.30; After the dyeing: +62.35; | −0.48; +10.76; | +10.40 +37.69 |
| | | Wash test: Dyeing result after 5 hours in demineralized water | +46.14; | +8.65; | +31.24 |
| 2.5 | 1,4-bis-(4,5-diamino-pyrazole-1-yl-methyl)-benzene: 4.28 g; 1,3-dimethyl-pyrazole-5-one: 1.12 g | warm yellow | Before the dyeing: +83.30; After the dyeing: +50.76 | −0.48; +32.70; | +10.40 +45.70 |
| | | Wash test: Dyeing result after 5 hours in demineralized water | +43.77; | +32.41; | +35.82 |
| 2.6 | 1,2-bis-(4,5-diamino-pyrazole-1-yl)-ethane: 3.52 g; 1,3-dimethyl-pyrazole-5-one: 1.12 g | medium blonde | Before the dyeing: +83.30; After the dyeing: +47.91; | −0.48; +12.25; | +10.40 29.50 |
| | | Wash test: Dyeing result after 5 hours in demineralized water | +40.04; | +12.68; | +20.85 |

The L*a*b* color values, given in the present examples, were determined with a Minolta, Type II Chromameter.

The "L" value represents the brightness (that is, the lower the "L" value, the greater is the intensity of the color), whereas the "a" value is a measure of the red portion (the red portion varies with the value of "a"). The "b" value is a measure of the blue portion of the color (the more negative the value of "b", the greater is the blue portion).

Unless stated otherwise, all percentages in the present application are percentages by weight.

What is claimed is:

1. An agent for oxidatively dyeing keratin fibers, said agent comprising a combination of at least one 4,5-diaminopyrazole derivative of formula (I), (II), (III) or a salt thereof with an organic or inorganic acid:

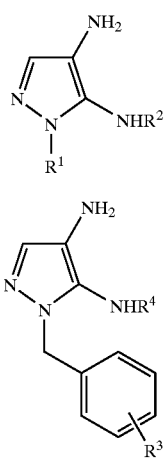

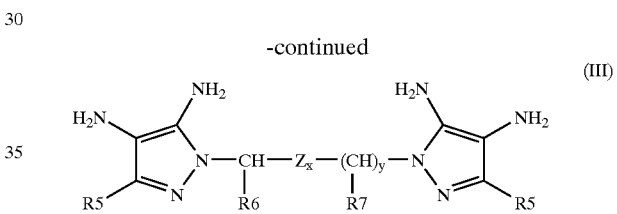

wherein $R^1$ represents hydrogen, a linear or branched $C_2$–$C_8$ alkyl group, an optionally substituted phenyl group or a linear or branched $C_2$–$C_4$ hydroxyalkyl group;

$R^2$ represen hydrogen, a linear or branched $C_1$–$C_8$ alkyl group, an optionally substituted phenyl group or a linear or branched $C_2$–$C_4$ hydroxyalkyl group;

$R^3$ represents a halogen atom, a linear or branched $C_1$–$C_4$ alkyl group or a linear or branched $C_1$–$C_4$ alkoxy group and $R^4$ represents hydrogen, a linear or branched $C_1$–$C_4$ alkyl group or a linear or branched $C_2$–$C_4$ hydroxyalkyl group;

$R^5$ represents hydrogen, a linear or branched $C_1$–$C_8$ alkyl group, a $C_1$–$C_4$ hydroxyalkyl group, a $C_1$–$C_4$ aminoalkyl group, a $C_1$–$C_8$ alkylamino group, a di($C_1$–$C_8$)alkylamino group, a $C_1$–$C_4$ alkylamino-($C_1$–$C_4$)alkyl group or a di($C_1$–$C_4$)alkylamino-($C_1$–$C_4$)alkyl group, an aryl group or a heteroaryl group;

$R^6$ and $R^7$ may be the same or different and, independently of each other, each represents hydrogen, a linear or branched $C_1$–$C_8$ alkyl group, an aryl group, a heteroaryl group, a carboxylic acid group, a carboxylic acid ester group, an optionally substituted carboxylic acid amide group, a hydroxy group or a $C_1$–$C_4$ hydroxyalkyl group or $R^2$ and $R^3$ jointly form an optionally substituted $C_1$–$C_8$ alkylene group;

Z is a $C_1$–$C_{10}$ alkyl diradical, which is optionally interrupted by a hetero atom, an aromatic diradical or a heteroaromatic diradical, which is optionally condensed with one or two benzene rings and/or substituted by a hydroxy group or a $C_1$–$C_6$ alkyl group, or a diradical of formula —Ar-(Alk)$_n$-Ar—, in which Ar is an optionally substituted aryl or heteroaryl group, Alk is a —CH₂ group and n is a whole number from 0 to 6; and x and y, independently of one another; are equal to 0 or 1; and
at least one pyrazol-5-one derivative of formula (IV), (V) or (VI), or a salt thereof with an organic or inorganic acid;

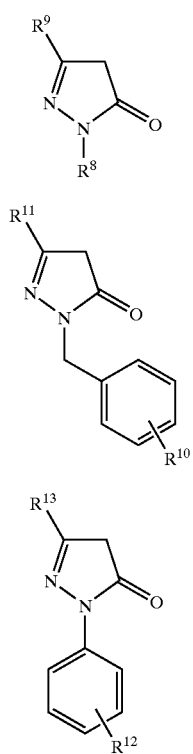

(IV)

(V)

(VI)

wherein $R^8$ represents a linear or branched $C_1$–$C_4$ alkyl group, a linear or branched $C_1$–$C_4$ alkoxy group, a linear or branched $C_1$–$C_4$ alkoxy-($C_1$–$C_8$)alkyl or a linear or branched $C_2$–$C_4$ hydroxyalkyl group; and
$R^9$ to $R^{13}$, independently of each other, each represents hydrogen, a linear or branched $C_1$–$C_4$ alkyl group, a linear or branched $C_2$–$C_4$ hydroxyalkyl group, a hydroxy group, an amino group, a linear or branched $C_1$–$C_4$ alkoxy group; a linear or branche $C_1$–$C_4$ alkoxy-($C_1$–$C_4$)alkyl or a linear or branched $C_1$–$C_4$-hydroxyalkylamino group.

2. The agent as defined in claim 1, wherein said at least one 4,5-diaminopyrazole derivative is selected from the group consisting of 4,5-diamino-1-(4'-methylbenzyl)-pyrazole; 4,5-diamino-1-(3'-methylbenzyl)-pyrazole; 4,5-diamino-1-(2'-methylbenzyl)-pyrazole; 4,5-diamino-1-(2'-hydroxyethyl)-pyrazole; 4,5-diamino-1-benzyl-1H-pyrazole; 4,5-diamino-1-ethyl-1H-pyrazole; 4,5-diamino-1-isopropyl-1H-pyrazole; 4,5-diamino-1-pentyl-1H-pyrazole; 4,5-diamino-1-(4'-methoxybenzyl)-1H-pyrazole; 4,5-diamino-1H-pyrazole; 4,5-diamino-1-(3'-methoxybenzyl)-1H-pyrazole; 4,5-diamino-1-(2'-methoxybenzyl)-1H-pyrazole; 4,5-diamino-1-(4'-chlorobenzyl)-1H-pyrazole; 4,5-diamino-1-(3'-chlorobenzyl)-1H-pyrazole; 4,5-diamino-1-(2'-chlorobenzyl)-1H-pyrazole; 4-amino-5-methylamino-1-(4'-methoxybenzyl)-1H-pyrazole; 4-amino-5-(2'-hydroxymethyl)amino-1-(4'-methoxybenzyl)-1H-pyrazole; 4-amino-5-methylamino-1-(2'-hydroxyethyl)-1H-pyrazole; bis-(4,5-diamino-pyrazole-1-yl)-methane; 1,2-bis-(4,5-diamino-pyrazole-1-yl)-ethane; 1,3-bis-(4,5-diamino-pyrazole-1-yl)-propane; 1,3-bis-(4,5-diamino-3-phenyl-pyrazole-1-yl)-propane; 2,3-bis-(4,5diaminopyrazole-1-yl)-propane-1-ol; N-benzyl-2,3-bis-(4,5-diamino-pyrazole-1-yl)-propionamide; 1,3-bis-(4,5-diaminopyrazole-1-yl) cyolohexane; 1,4-bis-(4,5-diaminopyrazole-1-yl-methyl)-benzene; 1,4-bis-(4,5-diamino-pyrazole-1-yl-methyl)-2,5-dimethoxy-benzene; 1,3-bis-(4,5-diaminopyrazole-1-yl-methyl)-benzene; 2,6-bis-(4,5-diaminopyrazole-1-yl-methyl)-4-methylphenol; 1,2-bis-(4,5-diaminopyrazole-1-yl-methyl)-benzene; 1,2-bis-(4,5-diamino-pyrazole-1-yl-methyl)-4,5-dimethoxybenzene; 2,3-bis-(4,5-diaminopyrazole-1-yl-methyl)-naphthalene; 2,3-bis-(4,5-diaminopyrazole-1-yl-methyl)anthracene; 9,10-bis-(4,5-diamino-pyrazole-1-yl-methyl)anthracene; 4,4'-bis-(4,5-diamino-pyrazole-1-yl-methyl)-biphenyl; 1,2-bis-[4-(4,5-diaminopyrazole-1-yl-methyl)-phenyl]-ethane; 2,5-bis-(4,5-diaminopyrazole-1-yl-methyl)-furan; 2,5-bis-(4,5-diaminopyrazole-1-yl-methyl)-thiophene; 2,8-bis-(4,5-diaminopyrazole-1-yl-methyl)-dibenzothiophene; 4,4'-bis-(4,5-diamino-pyrazole-1-yl-methyl)-[2,2]-bipyridyl and 1,2-bis-[6-(4,5-diaminopyrazole-1-yl-methyl)-pyridine-2-yl]-ethane; or is a salt thereof with an inorganic or organic acid.

3. The agent as defined in claim 1, wherein said at least one pyrazolone derivative is selected from the group consisting of 3-amino-1-phenylpyrazole-5-one, 3-methyl-1-phenylpyrazole-5-one, 1,3-dimethylpyrazole-5-one, 3methyl-1-(4-sulfphenyl)-pyrazole-5-one, 3-methyl-1-(2-hydroxyethyl)-pyrazole-5-one and 1-phenylpyrazole-5-one; or is a salt thereof with an inorganic or organic acid.

4. The agent as defined in claim 1, containing from 0.005 to 20 percent by weight of said at least one 4,5-diaminopyrazole derivative and from 0.005 to 20 percent weight of said at least one pyrazolone derivative.

5. The agent as defined in claim 1, further comprising oxidative dye precursors and/or substantive dyes.

6. The agent as defined in claim 1, further comprising developer and coupler substances.

7. The agent as defined in claim 6, containing from 0.01 to 20 percent by weight of said developer and coupler substances in each case.

8. The agent as defined in claim 5, containing said substantive dyes in an amount of from 0.01 to 10 percent by weight in each case.

9. A ready-for-use oxidation dye mixture having a pH of 3 to 11 and made by mixing the agent as defined in claim 1 with an oxidizing agent in a weight ratio of 5:1 to 1:3.

* * * * *